(12) United States Patent
Francis

(10) Patent No.: US 7,922,692 B2
(45) Date of Patent: Apr. 12, 2011

(54) VEIN SCOPE AND INJECTION SYSTEM

(75) Inventor: Raymond K. Francis, Cleveland, OH (US)

(73) Assignee: Raymond K. Francis, Cleveland, OH (US)

( * ) Notice: Subject to any disclaimer, the term of this patent is extended or adjusted under 35 U.S.C. 154(b) by 0 days.

(21) Appl. No.: 12/612,410

(22) Filed: Nov. 4, 2009

(65) Prior Publication Data

US 2010/0114023 A1   May 6, 2010

Related U.S. Application Data

(60) Provisional application No. 61/111,164, filed on Nov. 4, 2008.

(51) Int. Cl.
*A61M 5/00*   (2006.01)

(52) U.S. Cl. ............................... 604/116; 600/425
(58) Field of Classification Search .......... 600/423–426, 600/431–435; 604/116, 117, 151–155, 272
See application file for complete search history.

(56) References Cited

U.S. PATENT DOCUMENTS

| | | | | |
|---|---|---|---|---|
| 6,178,340 | B1 * | 1/2001 | Svetliza | 600/310 |
| 6,443,928 | B1 * | 9/2002 | Francis | 604/116 |
| 6,673,033 | B1 * | 1/2004 | Sciulli et al. | 604/67 |
| 2009/0076383 | A1 * | 3/2009 | Toews et al. | 600/432 |
| 2009/0318891 | A1 * | 12/2009 | Marcotte et al. | 604/510 |

* cited by examiner

*Primary Examiner* — Nicholas D Lucchesi
*Assistant Examiner* — Gerald Landry, II
(74) *Attorney, Agent, or Firm* — Fay Sharpe LLP; Brian E. Turung

(57) ABSTRACT

A medical device adapted to a view one or more body passageways in a body portion.

21 Claims, 4 Drawing Sheets

VEIN SCOPE AND INJECTION SYSTEM

The present invention claims priority on U.S. Provisional Patent Application Ser. No. 61/111,164 filed Nov. 4, 2008 entitled "Vein Scope And Injection System", which is fully incorporated herein by reference.

The present invention is directed to a medical device that is associated with locating body passageways in a organism, and more particularly to a medical device that can be used to locate one or more body passageways without having to first penetrate the skin of an organism, and even more particularly to a medical device that can be used to locate one or more body passageways beneath the skin of an animal or human and to guide a needle or other skin penetrating device to the located body passageway, and still even more particularly to a medical device that can be used to locate one or more body passageways beneath the skin of an animal or human and to guide a needle or other skin penetrating device to the located body passageways so that fluid can be inserted into and/or removed from the located body passageways, and still yet even more particularly to a medical device that can be used to locate one or more blood vessels beneath the skin of an animal or human and to guide a needle or other skin penetrating device to the located blood vessel so that fluid can be inserted into and/or removed from the located blood vessel.

BACKGROUND OF THE INVENTION

The present invention is an improvement over the view scope disclosed in U.S. Pat. No. 6,443,928, which is fully incorporated herein by reference.

Medical devices have long been developed to make one or more types of medical procedures easier, safer and more successful. Medical devices of known designs and configurations previously devised and utilized for the purpose of increasing the safety and efficiency are known to consist basically of familiar, expected, and obvious structural configurations, notwithstanding the myriad of designs encompassed by the crowded prior art which has been developed for the fulfillment of countless objectives and requirements. By way of example, U.S. Pat. No. 4,613,328 to Boyd discloses a biomedical injector apparatus; U.S. Pat. No. 5,137,518 to Mersch discloses an instantaneous vein entry indicator for intravenous needle; and U.S. Pat. No. 5,030,207 to Mersch et al. discloses an instantaneous vein entry indicator for an intravenous needle.

While these prior art medical devices fulfill their respective, particular objectives and requirements, the aforementioned patents do not describe a blood vessel scope and injection system that allows for the safe and efficient locating of blood vessels to thereby provide precise venous access.

The view scope developed by the present inventor and disclosed in U.S. Pat. No. 6,443,928, which is fully incorporated herein by reference, was designed to address this need in the medical field. The vein scope and injection system disclosed in the '928 patent was developed for the purpose of safely and to efficiently locate veins to thereby provide precise venous access. Although the vein scope and injection system disclosed in the '928 patent overcomes many of the problems associated with easily and effectively locating veins, such vein scope configuration had several design and configuration limitations.

Therefore, it can be appreciated that there exists a continuing need for a new and improved vein scope and injection system which can be used for safely and efficiently locating veins to thereby provide precise venous access. In this regard, the present invention substantially fulfills this need.

SUMMARY OF THE INVENTION

The present invention is directed to a medical device that can be used to locate one or more body passageways, more particularly to a medical device that can be used to locate one or more body passageways beneath the skin of an animal or human and to guide a needle or other skin penetrating device to the located body passageway, even more particularly to a medical device that can be used to locate one or more body passageways beneath the skin of an animal or human and to guide a needle or other skin penetrating device to the located body passageways so that fluid can be inserted into and/or removed from the located body passageways. The medical device of the present invention will be particularly described with reference to the use of the medical device for the location of blood vessels in an arm of a human and providing access to sch located blood vessel; however, it will be appreciated that the medical device of the present invention has broader applications and can be used to locate and/or provide access to other type of body passageways (e.g., lymph node, etc.); and/or can be used to located and/or provide access to one or more body passageways that are located in regions of the body other than an arm (e.g., leg, etc.); and/or locate and/or provide access to body passageways in organisms other than a human (e.g., cat, dog; etc.). As used herein, the term "body passageway" is defined to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, subarachnoid space, and central and peripheral nerve conduits, etc.).

In accordance with one non-limiting embodiment of the present invention, the medical device includes a monitor assembly, a support assembly and a needle handling assembly. The monitor assembly includes an image viewing surface in at least a portion of the upper surface of the monitor assembly. The monitor assembly also includes an image receiving surface on at least a portion of the bottom surface of the monitor assembly. The monitor assembly also includes electronic components capable of producing one or more images on the image viewing surface that is at least partially based on information received from the image receiving surface. The monitor assembly includes a housing that can be formed of one or more materials (e.g., plastic, metal, rubber, ceramic, etc.). Generally the one or more materials used to the form the house are durable materials so as to provide at least some protection to some of the more fragile electronic components located within the housing; however, this is not required. The support assembly is designed to at least partially support the monitor assembly and to at least partially support an arm and/or other body portion of a human when the monitor assembly is being used to locate one or more blood vessels and/or other body passageways under the skin of arm or other body portion. The support assembly can be designed to permanently or releasably secure the monitor assembly to the support assembly. The support assembly can be designed to allow or not allow the monitor assembly to be moveable relative to the support assembly. The support assembly can be formed of one or more materials (e.g., plastic, metal, rubber, ceramic, etc.). Generally the one or more materials used to the form the house are durable materials so as to provide at least some protection to some of the more fragile electronic components located within the housing;

however, this is not required. The needle handling assembly is designed to at least partially support and/or hold a needle, syringe, or other skin penetrating device. The needle handling assembly is generally connected to the monitor assembly; however, this is not required. The needle handling assembly is designed to permanently or releasably secure a needle, syringe, or other skin penetrating device. The needle handling assembly is also designed to enable a user to properly orient a needle, syringe, or other skin penetrating device relative to a body portion that is at least partially positioned between at least a portion of the monitor assembly and the support assembly so as to enable the user to guide at least a portion of the needle, syringe, or other skin penetrating device into the skin and to a desired body passageway underneath the skin.

In accordance with another and/or alternative non-limiting embodiment of the present invention, the support assembly of the medical device includes a base portion and at least one side portion that extends upwardly from the upper surface of the base portion. The upper surface of the base portion is generally a flat and smooth surface to enable a body portion to be easily positioned on the upper surface of the support assembly; however, it can be appreciated that the upper surface can include non-smooth regions and/or include non-flat regions. The base portion is generally formed of a single piece of material; however, it can be appreciated that the base portion can be formed of a plurality of pieces that can be connected together by a hinge and/or other type of connection arrangement. In one non-limiting embodiment, the support assembly includes a base portion and a side portion that is connected to the base portion. The side portion is generally designed to be connected at or near a side edge of the base portion and extend upwardly from the upper surface of the base portion. The side portion can be formed of the same or different material as the base portion. The side portion can be fixed in a relative portion relative to the base portion or be adjustable relative to the base portion. The side portion can be connected to the base portion in a manner that allows the base portion to be collapsed or folded onto the base portion for purposes of storage; however, this is not required. Generally the side portion fowls an angle with the base portion of about 45°-120°, and more typically about 60°-90°. The support assembly can include a second side portion position at or near the edge opposite the edge that the other side portion is located; however, this is not required. When the support assembly only includes one side portion, the support assembly profiled is generally L-shaped, and when the support assembly includes two side portions, the support assembly profile is generally U-shaped. Generally the side portion extends about 2-8 includes above the upper surface of the base portion. Generally the inner surface of the side portion has a smooth surface; however, this is not required. In another and/or alternative non-limiting embodiment of the invention, the base portion includes a recessed portion on the upper surface of the base portion. When the recess portion is included in the base portion, the recess portion is designed to fascinate in the proper positioning of a body part on the base portion when using the medical device of the present invention. In one non-limiting aspect of this embodiment, the recessed portion has a generally concave profiled that extends partially or fully along the longitudinal length of the base portion.

In accordance with another and/or alternative non-limiting embodiment of the present invention, the monitor assembly is connected to the support assembly in a manner that enables the monitor assembly to be raised and/or lowered relative to the upper surface of the base portion of the support assembly and/or to be moveable along the longitudinal length of the base portion of the support assembly so as to facilitate in the positioning of a body portion between a portion of the monitor assembly and the base portion of the support assembly and/or to orient the monitor system relative to a body portion that is positioned on the base portion of the support assembly. In one non-limiting embodiment of the invention, the monitor assembly is connected to the support assembly in a manner that enables the monitor assembly to be raised and/or lowered relative to the upper surface of the base portion of the support assembly. The monitor assembly can be designed to be moveable in a generally tangential plane relative to the upper surface of the base portion and/or be connected to the support assembly such that the monitor can be pivot or rotated up from and/or down toward to the upper surface of the support assembly. In one non-limiting aspect of this embodiment, the monitor assembly is designed to be moveable in a generally tangential plane relative to the upper surface of the base portion; however, this is not required. Many different arrangements can be used to accomplish such movement of the monitor assembly relative to the upper surface of the base portion of the support assembly. In one non-limiting design, the support assembly and/to monitor assembly includes one or more legs or pins that enable monitor assembly to be moveable in a generally tangential plane relative to the upper surface of the base portion. In another and/or alternative non-limiting aspect of this embodiment, the monitor assembly is designed to pivot upwardly and downwardly relative to the upper surface of the base portion; however, this is not required. In one non-limiting design, the support assembly and/to monitor assembly includes one or more hinges that enable monitor assembly to pivot. In another and/or alternative non-limiting embodiment of the invention, the monitor assembly is connected to the support assembly in a manner to cause the monitor assembly to be biased toward the upper surface of the base portion; however, this is not required. The biasing action can be caused by various arrangements (e.g., spring, compression component, fluid pressure, magnet, etc.). In still another and/or alternative non-limiting embodiment of the invention, the monitor assembly is connected to the support assembly in a manner that enables the monitor assembly to be moveable along the longitudinal length of the base portion of the support assembly; however, this is not required. Various arrangements can be used to achieve such relative movement (e.g., wheel and slot arrangement, tongue and groove arrangement, ratchet arrangement, etc.). In one non-limiting designed, the support assembly includes spaced parallel guide rails that form a groove for a wheel or tongue arrangement to move within the guide rails and enable the monitor assembly to be moveable along the longitudinal length of the base portion of the support assembly.

In accordance with still another and/or alternative non-limiting embodiment of the present invention, the monitor assembly includes one or more image viewing surfaces on the upper surface of the monitor assembly that enables a user to view one or more types of information. Generally the upper surface of the monitor assembly includes at least one primary display that is used by a user to view one or more body passageways in a body portion. The upper face can also include one or more switches or buttons to operate one or more features of the monitor assembly (e.g., power button, brightness button, zoom button, image position button, image color button, image contrast button, image resolution button, print button, send button, menu button, image positioning button, program button, save button, sound button, alarm button, etc.); however, it can be appreciated that one or more buttons or switches can be located on other regions of the monitor assembly. As can be appreciated, the image viewing surface can include touch screen features that include one or more of these features, thus reducing or eliminating the number of switches or buttons on the monitor assembly. Also or alternatively, the upper face can include one or more additional displays to provide information to the user (e.g., power on state, power off state, battery charge state, battery power level, etc.); however, it can be appreciated that one or more of the other displays can be located on other regions of the monitor assembly. As can be appreciated, the image viewing surface can include touch screen features that include one or more of these features, thus reducing or eliminating the number of other displays present on the monitor assembly. Also or alternatively, the main viewing screen can display one or more features of the monitor assembly in addition to information about a body part positioned between a portion of the monitor assembly and the support assembly. For instance, in addition to the one or more features previously listed above, the main view screen can display information such as, but not limited to, an internet status, medical facility information, patient history, procedure history, medical device service information, body passageway maps, electronic malfunctions, user instructions, real-time needle assembly use, recommended needle approach for access of a body passageway, error warnings, time and date information, usage information, body portion temperature, duration of signal generation, duration warning for signal generation on body portion, monitor assembly orientation and position information relative to body portion and/or support assembly, etc.). As can be appreciated, the upper face of the monitor assembly can include more than one display. The type of display used on the monitor assembly is non-limiting (e.g., diode display, LED display, LCD display, OLED display, DLP display, LcoS display, SED display, FED display, Penetron display, plasma display, cathode ray tube display, etc.). When the monitor assembly includes two or more displays, the same or different type of display can be used. The profile of the upper surface of the monitor assembly is non-limiting.

In accordance with yet another and/or alternative non-limiting embodiment of the present invention, the monitor assembly includes one or more image receiving surfaces at or near the lower surface of the monitor assembly. The one or more image receiving surfaces are designed to receive information from a body portion that is positioned at least partially between the support assembly and the monitor assembly. The received information is generally conveyed to one or more components of the medical device (typically located on or in the monitor assembly; however, not required) wherein such information is process so as to be displayed on one or more of the displays on the upper surface of the monitor assembly. The type of electronics included in the monitor assembly to receive and process the received information is non-limiting. As can be appreciated, the support assembly on or near the upper surface can also or alternatively include one or more image receiving surfaces; however, this is not required. The monitor assembly and/or support assembly is generally designed to generate a signal that at least partially penetrates a body portion that is positioned at least partially between the monitor assembly and the support assembly so that one or more of the image receiving surfaces can receive the signal for use in generating an image on one or more of the displays; however, this is not required.

In accordance with still yet another and/or alternative non-limiting embodiment of the present invention, the lower surface of the monitor assembly can be contoured so as to facilitate in the positioning of at least a portion of a body part at least partially between the monitor assembly and the support assembly; however, this is not required.

In accordance with another and/or alternative non-limiting embodiment of the present invention, the monitor assembly can include one or more handles, latches etc. to lift, position, move and/or maintain the monitor assembly relative to the support assembly; however, this is not required.

In accordance with still another and/or alternative non-limiting embodiment of the present invention, the monitor assembly and/or support assembly can include a power supply that is rechargeable or non-rechargeable. In one embodiment of the invention, the monitor assembly and/or support assembly includes one or more solar batteries and/or fuel cells to at least partially provide power to the medical device; however, this is not required.

In accordance with yet another and/or alternative non-limiting embodiment of the present invention, the needle handling assembly is designed to support and position a needle, syringe, or other type of body penetrating device to a desired position on the body portion that is at least partially positioned between at least a portion of the support assembly and the monitor assembly. One non-limiting feature of the medical device of the present invention is to display one or more body passageways in the body portion that is at least partially positioned between at least a portion of the support assembly and the monitor assembly and to enable a user to use the needle handling assembly is designed to guide the needle, syringe, or other type of body penetrating device to a located body passageway. The needle handling assembly can be designed to enable a user to move and position the needle, syringe, or other type of body penetrating device toward the desired body passageway and/or away from the desired body passageway. The needle handling assembly can be designed to enable a user to move and position the needle, syringe, or other type of body penetrating device along two or more axes (e.g., x-axis, y-axis, z-axis) so that the user can position the needle, syringe, or other type of body penetrating device at the desired penetration point on the body portion. In one non-limiting embodiment or the invention, the needle handling assembly is designed to removably connect the needle, syringe, or other type of body penetrating device; however, this is not required. The design and configuration of the needle handling assembly is non-limiting. Generally the needle handling assembly is connected to the monitor assembly; however, it can be appreciated that a portion or all of the needle handling assembly is connected to the support assembly. In one non-limiting design, the needle handling assembly is connected to the monitor assembly. The needle handling assembly includes one or more slide members that are designed to move relative to the body of the monitor assembly. A needle, syringe, or other type of body penetrating device is removably connected to the needle handling assembly and the needle handling assembly is designed to enable a user to move the needle, syringe, or other type of body penetrating device toward the body portion that is at least partially positioned between at least a portion of the monitor assembly and the support assembly while one or more body passageways are being displayed on the upper surface of the monitor assembly. In this manner, precise viewing and access of a body passageway is facilitated during operation and use of the medical device of the present invention.

It is therefore one non-limiting object of the present invention to provide a new and improved medical device which has all of the advantages of the prior art medical devices of known designs and configurations and none of the disadvantages.

It is another and/or alternative non-limiting object of the present invention to provide a new and improved medical device which may be easily and efficiently manufactured and marketed.

It is still another and/or alternative non-limiting object of the present invention to provide a new and improved medical device which is of durable and reliable constructions.

It is yet another and/or alternative non-limiting object of the present invention to provide a new and improved medical device which is susceptible of a low cost of manufacture with regard to both materials and labor, and which accordingly is then susceptible of low prices of sale to the consuming public, thereby making such medical device economically available to the buying public.

It is still yet another and/or alternative non-limiting object of the present invention to provide a new and improved medical device for safely and efficiently locating body passageways to thereby provide precise access to such body passageways.

It is another and/or alternative non-limiting object of the present invention to provide a new and improved medical device which includes a monitor assembly that includes an image viewing surface and an image receiving surface, a support assembly that is designed to support the monitor assembly and which support assembly includes a base portion and at least one side portion, and a needle handling assembly that is designed to supports a needle, syringe, or other type of body penetrating device and is able to position and guide the needle, syringe, or other type of body penetrating device toward the body portion that is at least partially positioned between at least a portion of the monitor assembly and the support assembly while one or more body passageways are being displayed on the upper surface of the monitor assembly.

Several other features of the medical device of the present invention are set forth as follows:

The medical device simplifies and/or improves the manner in which difficult to access body passageways are accessed.

The medical device can be less painful to a patient when a body passageway is accessed.

The monitoring assembly (e.g., display, etc.) can be designed to enable the viewing of peripheral veins under the skin.

One or more components of the medical device (e.g., display, image processor, etc.) can be designed to be at least partially powered by solar energy and/or fuel cell.

The monitoring assembly (e.g., display, etc.) can be designed to view deeper body passageways (e.g., arteries, varicose veins, etc.).

The support assembly which mounts the monitoring assembly can be adjustable to accommodate babies, children and all sized adults.

The needle handling assembly can include a disposable portion of safety and sanitary purposes.

The needle handling assembly can be designed allow a user to move a needle, syringe, or other type of body penetrating device in two or more axes so that the a needle, syringe, or other type of body penetrating device can be properly positioned to properly access a body passageway.

The monitoring assembly (e.g., display, etc.) can be designed to be removable from the support assembly so that the monitor assembly can be easily transported to other locations and connected to other support assemblies.

The monitoring assembly (e.g., display, etc.) can be designed to be removable from the support assembly so that the monitor assembly can be detachably connected to a pole and/or other transport device to facilitate in transporting the monitor assembly to other locations.

The support assembly can be collapsible for easy transport and/or storage.

The monitoring assembly (e.g., display, etc.) can be designed to view foreign objects under the skin.

These and other advantages will become apparent to those skilled in the art upon the reading and following of this description taken together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE INVENTION

Figure 1:
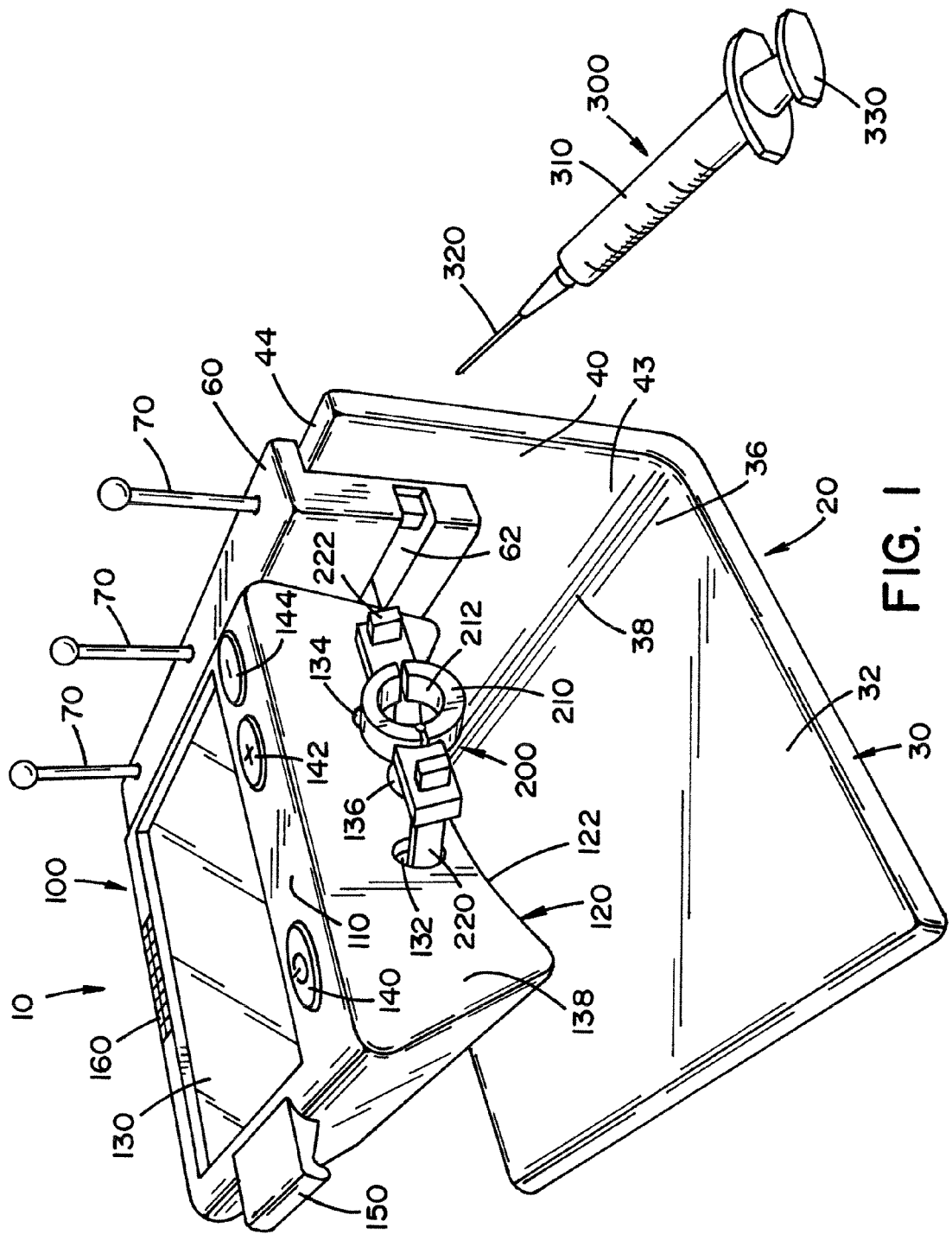
FIG. 1 is an elevation view of the medical device in accordance with the present invention.

Referring now to the drawings wherein the showings are for the purpose of illustrating embodiments of the invention only and not for the purpose of limiting the same, FIGS. 1-5 disclose a medical device in accordance with the present invention. The medical device 10 of the present invention is designed to generate an image of one or more body passageways A in a body portion B. The invention will be particularly described with reference to the viewing of blood vessels in an arm; however, it will be appreciated the medical device can view other or additional types of body passageways in the arm and/or other types of body portions (e.g., leg, fingers, toes, etc.).

Figure 2:
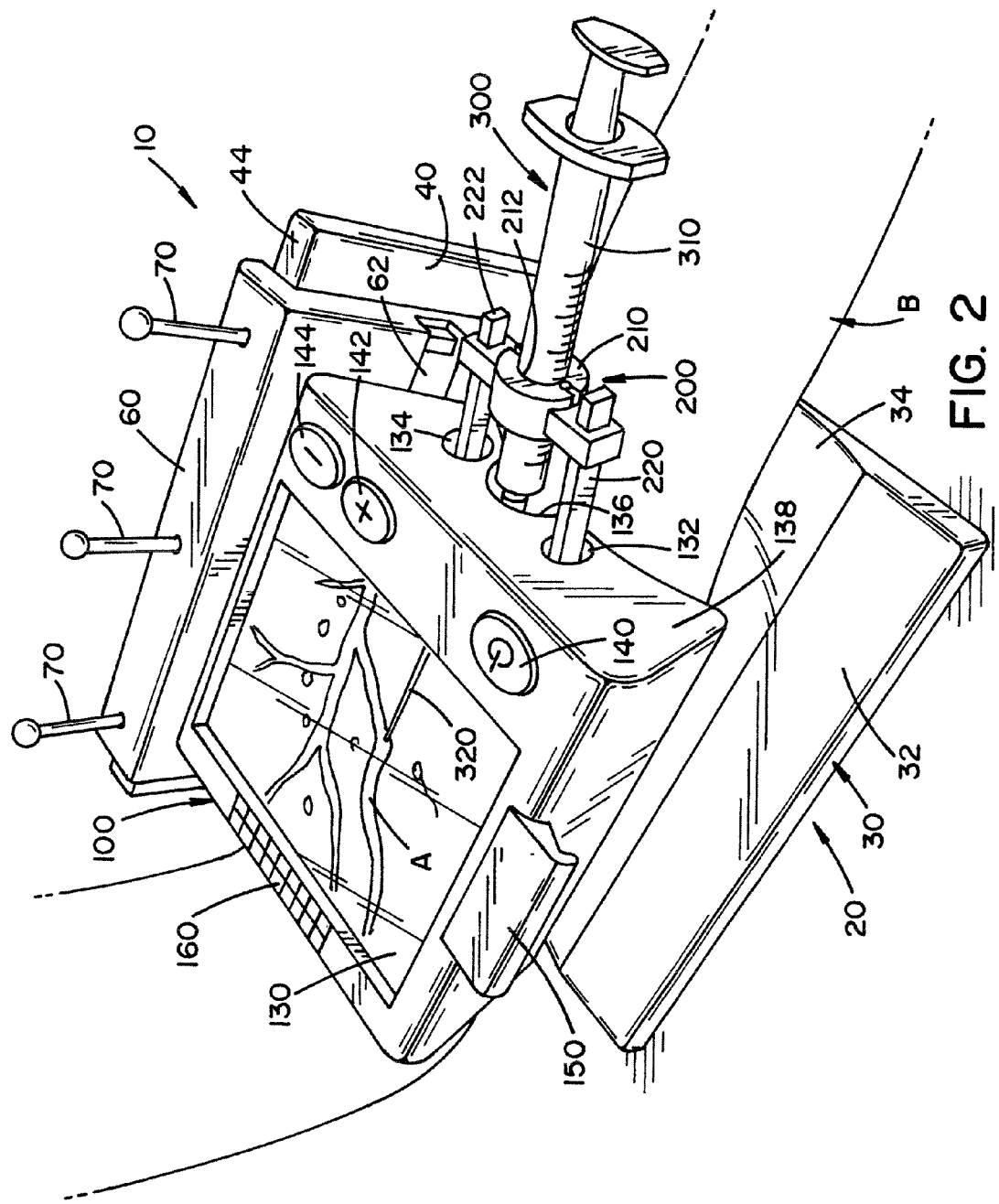
FIG. 2 is an elevation view of an alternative embodiment of the medical device in accordance with the present invention that shows the operation of the medical device when an portion of an arm is viewed by the medical device.

Referring now to FIG. 1, the medical device 10 includes three primary components, namely a support assembly 20, a monitor assembly 100, and a needle handling assembly 200. The support assembly 20 includes a base portion 30 and a side wall 40. The base portion includes an upper surface 32 which can include a contoured portion 34 that runs along the longitudinal length of the base portion. The contoured portion is an optional feature and is designed to facilitate in positioning arm B in the base portion. The contoured portion is illustrated in FIG. 2, but is not illustrated in FIG. 1.

Side edge 36 of the base portion and a bottom edge 42 of the side wall can be connected by a hinge, not shown, so that the base portion and side wall can be collapsed onto one another to facilitate in storage; however, this feature is an optional feature. As can be appreciated, the side wall and base portion can be connected together in other locations. As can also be appreciated, the base portion and side wall can be connected together so that such components cannot be collapsible. It can also be appreciated that the base portion and side wall can be connected together in manner other than a hinge so that the portions can be collapsible.

As illustrated in FIG. 1, a curved transition 38 can exist between the side wall and the base portion; however, this is not required. The edges of the side wall and base portion can be rounded or tapered as illustrated in FIGS. 1 and 2; however, this is not required.

FIG. 1 illustrates the support assembly as including only a single side wall 40. As can be appreciated, the support assembly can include a second side wall, not shown, that oppositely faces side wall 40. Generally the structure of the second side wall is the same as side wall 40; however, this is not required. In addition, the arrangement in which second side wall is connected to base portion 30 can the same or different from the connection arrangement between side wall 40 and base portion 30.

The materials used to form the support assembly are non-limiting. Generally the support assembly is formed of durable materials such as, but not limited to, metal, plastic, composite material, etc.

As illustrated in FIG. 1, a support bracket 60 is connected to the top 44 of the side wall 40. The support bracket is designed to be connected to the monitor assembly 100. The support bracket is illustrated as being mounted to the side wall such that the support bracket can move upwardly and downwardly relative to the base portion of the support assembly. As can be appreciated, the support bracket can be mounted to the side wall in other ways so that the support bracket can move in other or additional ways relative to the side wall (e.g., a pivot movement, movement along the longitudinal axis of the side wall, etc.) or be mounted to that there is no relative movement between the side wall and the support bracket. Referring again to FIG. 1, support bracket 60 is mounted to the side wall by use of one or more legs or pins 70. The support bracket can be designed to side up and down the one or more legs or pins, and/or the one or more legs or pins can move downwardly and upwardly relative to the side wall. The support bracket can be designed to be biased in a downward positioned by one or more biasing elements (e.g., spring, etc.), now shown; however, this is not required. The upward and downward movement of the support bracket enables the monitor assembly to be moved upwardly and downwardly relative to the base portion of the support assembly so that the body portion can be easily and conveniently positioned between the monitor assembly and the support assembly and removed from the monitor assembly and the support assembly.

Leg or pins 70 can be connected to the monitor assembly and/or support assembly in a manner that allows the monitor assembly to be detached from the side wall of the support assembly. Although not shown, it can be appreciated that when the monitor assembly is detached from the support assembly, the monitor assembly could be connected to some other type of support assembly (e.g., pole, bed tray, etc.) to enable the monitor device to be used in other locations (e.g., hospital, medical facility, etc.) and/or on other location of a patient (e.g., head, back, hip, etc.); however, such alternative mounting of the medical device is not required.

Referring again to FIG. 1, the support bracket includes a position slot 62 along at least a portion of the longitudinal length the support bracket. The position slot can be used to position the monitor assembly in a plurality of positions along the longitudinal length of the base portion and side wall of the support assembly; however, this is not required. As can be appreciated, other or additional arrangements can be used to position the monitor assembly in a plurality of positioned along the longitudinal length of the base portion and side wall of the support assembly. The longitudinal positioning of the monitor assembly can be used to better position the monitor assembly on the body portion when the body portion is positioned between the monitor assembly and the support assembly.

When the support assembly includes two side walls, not shown, a support bracket can be positioned on both side walls so that each of the side walls at least partially support the monitor assembly; however, this is not required. When two support brackets are used, the structure and function of the two support brackets is generally similar; however, this is not required. As can be appreciated, when two side walls are used, the support bracket 60 and side wall 40 as discussed with regard to FIG. 1 can be used, and the second side wall can merely be use to open and close a cavity formed by the base portion, the two side walls and lower surface of the monitor assembly; however, this is not required. For this non-limiting arrangement, the movement of the second side wall to an open position enables a body portion to be inserted into or removed from the medical device, and the second side wall in the closed positioned facilitates in maintaining the body portion in the medical device and can also be used to at least partially support the monitor assembly. The upward movement, downward movement and/or longitudinal movement of the monitor assembly would primarily be facilitated by side wall 40 as illustrated in FIG. 1. As can be appreciated, many other configurations involving the use of two side walls on the support assembly can be used.

Figure 3:
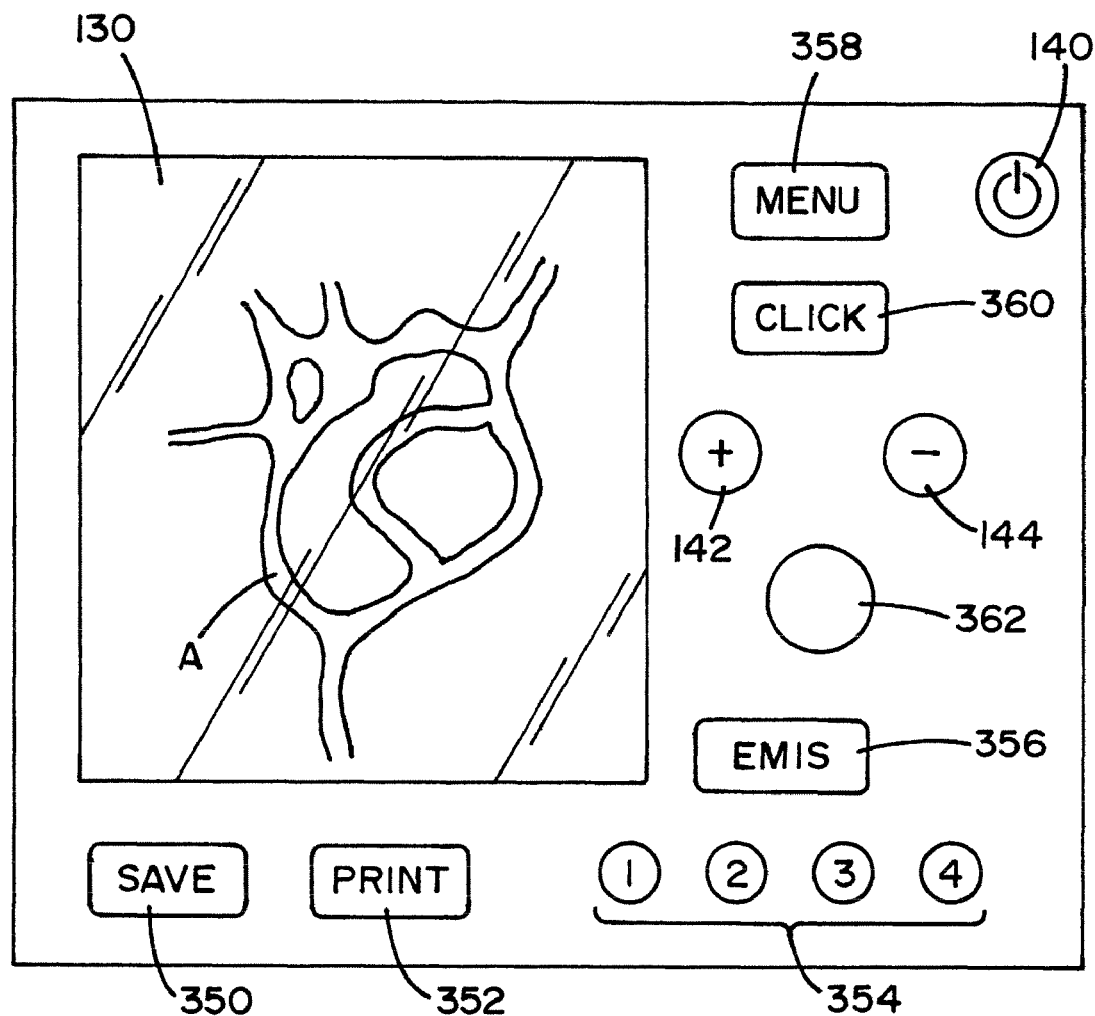
FIG. 3 is an alternative embodiment of the upper surface of the monitor assembly.

As illustrated in FIG. 1, the monitor assembly 100 includes an upper surface 110 and a lower surface 120. The upper surface includes a display screen 130 and one or more buttons 140, 142, 144. The upper surface of the monitor assembly generally includes a single display screen; however, it can be appreciated that more than more display screen can be present on the upper surface of the monitor assembly. The one or more buttons on the upper surface can be used to control a variety of functions of the monitor assembly. As illustrated in FIG. 1, button 140 is a power button that is used to power on and off the display screen 130. Buttons 142 and 144 are display zoom buttons to increase and decrease the image being displayed on the display screen. As can be appreciated, additional buttons can be present on the upper surface of the monitor assembly and/or be located in other locations on the monitor assembly (e.g., side surface, lower surface, etc.) and/or can be used to perform other or additional functions. For instance, FIG. 3 illustrates the upper surface of the monitor assembly generally having additional buttons. These additional button includes a save button, a print button, four programmable function buttons, emissivity adjustment button, two image zoom buttons, a power button, a menu button, a click or image activation button, and a rotating joystick to adjust the image position on the display screen. As can be appreciated, other or additional button can be located on the upper surface of the monitor assembly. As can also be appreciated, the display screen can be a touch screen that enables a user to operate, control and/or access one or more features of the medical device. As such a few or all of the buttons illustrated in FIGS. 1 and 3 can be eliminated form the upper surface of the monitor assembly and be accessed via the touch screen. As can also be appreciated, one or more buttons can be positioned on other locations of the monitor assembly and/or be positioned on the support assembly.

The display screen 130 can be any type of screen (e.g., LCD, etc.). Generally, the type of display screen selected has low power consumption and can generate an image having a desired resolution and contrast; however, this is not required. The display screen can be a color screen or a black and white screen. The display can be designed to highlight various features (e.g., highlight body passageways, highlight nerves, highlight bones, etc.); however, this is not required. The shape of the display screen is non-limiting. As illustrated in FIGS. 1 and 2, the display screen is polygonal shaped. The size of the display screen is also non-limiting; however, the size of the display screen is generally selected to cover more than a majority of the upper surface of the monitor assembly; however, this is not required.

The monitor assembly can include a handle 150; however, this is not required. The handle can be used to facilitate in the upward and downward movement, and/or longitudinal movement of the monitor assembly relative to the upper surface of the base portion of the support assembly.

The monitor assembly and/or support assembly can include a friction or locking arrangements that can be used to permanently or temporarily lock the position of the monitor assembly relative to the support assembly; however, this is not required.

The lower surface 120 of the monitor assembly 100 can include a contoured region 122 at least partially along the longitudinal length of the monitor assembly; however, this is not required. The contoured region 122 on the monitor assembly, when used, has a similar function as the contoured region on the base portion of the support assembly, when used.

The medical device includes one or more signal generating components that are designed to send a signal to a body portion that is located between the monitor assembly and the support assembly. This signal that is generated by the one or more signal generating components is designed to at least partially penetrate the surface of the body portion and then be at least partially collected by one or more signal receiving devices. The collected signal is then processed by one or more electronic components in the medical device so that an image can be generated and displayed on the one or more display screens on the upper surface of the monitor assembly. The type of signal that is generated is non-limiting. As can be appreciated, two or more different types of signals can be generated, two or more frequencies of signals can be generated, and/or two of more signals having different durations can be generated. Generally the type of signal generated is an electromagnetic signal (e.g., radio waves, Terahertz radiation, IR radiation, Visible light, Ultraviolet light, X-rays, etc.) and/or ultrasonic waves. In one non-limiting application of the present invention IR radiation is generated by the medical device. The signal generating devices and the signal receiving devices can be located in one or more locations on the medical device. Generally, the signal generating devices and the signal receiving devices are located on the monitor assembly and/or the support assembly. In one non-limiting design, the signal generating devices and the signal receiving devices are located on the monitor assembly. When the signal generating devices and/or the signal receiving devices are located on the monitor assembly, the signal generating devices and/or the signal receiving devices are generally located at or near the lower surface of the monitor assembly; however, this is not required. When the signal generating devices and/or the signal receiving devices are located on the support assembly, the signal generating devices and/or the signal receiving devices are generally located at or near the upper surface of the base portion of the support assembly; however, this is not required. In another non-limiting design, the medical device includes a plurality of signal generating devices so that a desired image of the body passageway in the body portion and the body penetrating device can be viewed on the one or more displays. In accordance with this non-limiting design, at least two and generally two or three signal generating devices are included in the medical device; however, more than three signal generating devices can be used.

As illustrated in FIGS. 1 and 2, the lower surface of the monitor assembly includes both the signal generating device(s) and the signal receiving device(s) for the medical device. The base portion of the support assembly can by formed of and/or coated with a material that facilitates in the reflecting of the signal generated from the monitor assembly back to the monitor assembly; however, this is not required. The upper surface of the base portion of the support assembly and/or the lower surface of the monitor assembly can be shaped to facilitate in the reflecting and/or receiving of the signal generated from the monitor assembly back to the monitor assembly; however, this is not required. The types of electronic components used to generate and/or receive a signal are non-limiting. The operation and use of such components is generally known in the art and will not be described in detail herein.

The signal processing components that are used to process the received signal and then generate a display signal that can be displayed on one or more of the displays on the upper surface of the monitor assembly are non-limiting. The signal processing components can be used to enhance and/or modify the received signal so that a desired image is displayed on the one or more displays. Generally the signal processing components include a microprocessor and a video processor; however, this is not required. The signal processing components can be located in one or more locations on the medical device. Generally, the signal processing components are located on the monitor assembly and/or the support assembly. In one non-limiting design, the signal processing components are located on the monitor assembly. As illustrated in FIG. 1, the monitor assembly includes the signal processing components.

The medical device can include a power source and/or be designed to be powered by an external power source. When the medical device includes a power source, such power source is generally in the form of a battery; however, other or alternative power sources can be used (e.g., solar cells, fuel cells, etc.). The location of the power source is non-limiting. Generally, the power source is located in the support assembly and/or the monitor assembly. As illustrated in FIG. 1, the monitor assembly includes a power source in the form of one or more batteries. The power source may or may not be a rechargeable power source. When the medical device is designed to be powered by an external power source, the medical device can include a plug and/or power connector positioned on the monitor assembly and/or the support assembly. The medical device can include one or more solar cells 160 to at least partially provide power to the medical device. When one or more solar cells are used, the one or more solar cells can be located on the monitor assembly and/or the support assembly. As illustrated in FIG. 1, a solar cell 160 is located on a portion of the upper surface of the monitor assembly.

The medical device can include additional electronics (e.g., video connections, USB connections, fire wire connections, ethernet connections, wireless internet components, telephone jack, wireless telephone components, GPS, etc.); however, this is not required. These additional electronics can be located on the monitor assembly and/or the support assembly. Additionally, the electronic components of the medical device can be used to operate software programs (e.g., Windows Mobile software, Google maps, software used by a medical facility, etc.) and/or allow for programs to be created on run on the medical device; however, this is not required.

Referring again to FIG. 1, there is illustrated a needle handling assembly 200 that is connected to medical assembly 100. The needle handling assembly is designed to position a body passageway penetration device (e.g., a needle, a catheter, a syringe, an IV, a tube, etc.) relative to the body portion that is positioned between the monitor assembly and the support assembly and then enable a user to penetrate the body portion with the end of the body passageway penetration device and access the desired body passageway (e.g., blood vessel, etc.) that is located in the body portion (e.g., arm, leg, etc.). The needle handling assembly includes a mount 210 that is designed to at least partially support a passageway penetration device. The mount 210 includes a mount opening 212 that is designed to receive the passageway penetration device. As illustrated in FIGS. 1 and 2, the passageway penetration device is in the form of a syringe 300. The syringe includes a tubular body 310 and a needle 320 that is connected to the end of body 310. A plunger 330 is positioned in body 310 and is designed to inject fluid in body 310 through needle 320 and/or draw fluid through needle 320 into body 310. The operation and use of syringe 300 is well known in the art and will not be described further. As illustrated in FIG. 2, body 310 is at partially inserted into mount 210 so that syringe 300 is securely connected to the needle handling assembly and that the syringe is properly oriented in the needle handling assembly. Generally, the syringe is designed to be releasably connected to mount 210; however, this is not required. Mount 210 forms a friction connection with the syringe and/or includes a clamping arrangement, not shown, to connect the syringe to mount 210.

Mount 210 is illustrated as being connected to two rods or legs 220, 222 that are in turn connected to the monitor assembly. The monitor assembly is illustrated as including two openings 132, 134 in one side 138 of the monitor assembly. These two openings are illustrated as receiving legs 220, 222. Side 138 also includes a semi-circular recessed portion 136 that is designed to provide space for the needle and/or body of the syringe to be positioned relative to a body portion that is positioned between the monitor assembly and the support assembly. As can be appreciated, openings 132, 134 and recessed portion 136 can have different shapes and/or configuration. Also, it will be appreciated that openings 132, 134 and recessed portion 136 are optional components. The arrangement in which rods or legs 220, 222 are connected to the monitor assembly is non-limiting.

The needle handling assembly is designed to enable a user to move the passageway penetration device in multiple axes. As such, the needle handling assembly enables a user to move the passageway penetration device toward and away from a body portion (first axis of movement), enables a user to move the passageway penetration device upwardly and downwardly relative to the body portion (second axis of movement), and/or enables a user to move the passageway penetration device sideward relative to the body portion (third axis of movement). As such, the needle handling assembly enables a user to move the passageway penetration device in two or three axis of movement relative to the body portion. As illustrated in FIG. 2, syringe 300 is connected in opening 212 of mount 210 and is tilted slightly downward toward the body portion. Also, leg 220 is illustrated as being inserted farther into opening 132 than leg 222 in opening 134, thus illustrating that the syringe has be moved to the right of center of the monitor assembly. Mount 210 can be designed to be removably connected to legs 220 and 222, and/or legs 220, 222 can be designed to be removably connected to the monitor assembly so that the mount and/or legs can be disposed of for sanitary purposes; however, this is not required.

Figure 4:
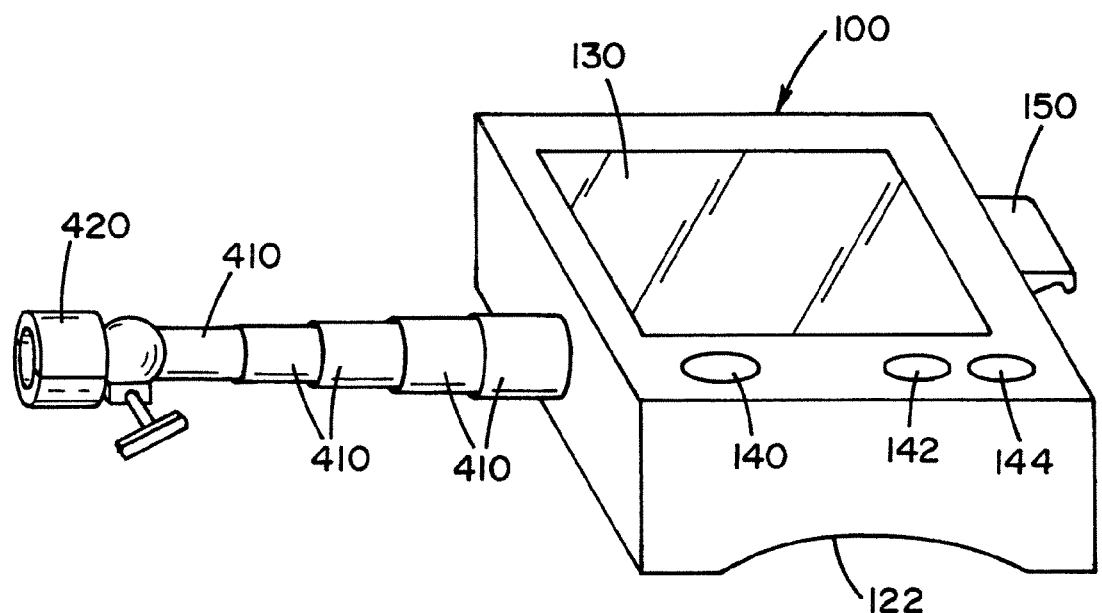
FIG. 4 is an alternative embodiment of a needle handling assembly.
Figure 5:
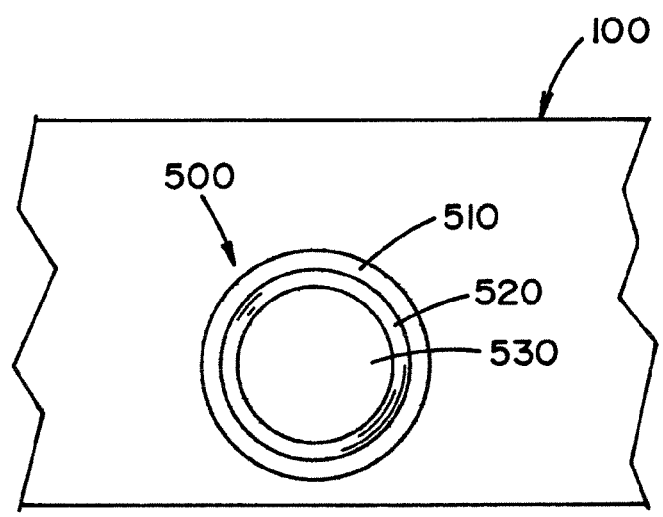
FIG. 5 is another alternative embodiment of a needle handling assembly.

As is appreciated, FIGS. 1 and 2 illustrate just one of several arrangements that can be used to enable a user to move the passageway penetration device in multiple axes. FIGS. 4 and 5 illustrate non-limiting alternative configurations that enable a user to move the passageway penetration device in multiple axes.

FIG. 4 illustrated a telescopic mount arrangement 400. The telescopic mount arrangement 400 includes a plurality of telescopic receiving portions 410. The number of such telescopic receiving portions is non-limiting. The front end portion of the telescopic mount arrangement is connected to the monitor assembly. The back end portion of the telescopic mount arrangement is connected to an adjustable clamp 420. The front end portion of the telescopic receiving portions can be removably connected to the monitor assembly so that the telescopic mount arrangement can be removed from the monitor assembly for sanitary purposes; however, this is not required. The adjustable clamp is connected to the back end of the telescopic mount arrangement in a manner that enables the adjustable clamp to swivel within one or more planes. The plurality of telescopic receiving portions can be connected together to enable one or more of the telescopic receiving portions to rotate relative to another telescopic receiving portion; however, this is not required. The adjustable clamp can be designed to be releasably connected to the back end of the telescopic mount arrangement; however, this is not required. The adjustable clamp is designed enable a syringe or other type of body penetrating device to be connected to the adjustable clamp. The adjustable clamp can be designed to releasably connect a syringe or other type of body penetrating device to the adjustable clamp; however, this is not required.

FIG. 5 illustrate a ball and socket arrangement 500. The ball and socket arrangement 500 includes a socket 510 and a ball 520 that is positioned in the socket. The socket can be formed in the side wall of to monitor assembly as illustrated in FIG. 5, or be connected in some other matter to the monitor assembly. The socket is designed to at least partially encircle and retain ball 520 within the socket. The ball and socket are sized and shaped to enable the ball to move within the socket. Generally the socket is formed in or connected to the monitor assembly such that the socket does not move relative to the monitor assembly; however, it can be appreciated that the socket can be formed in or connected to the monitor assembly to allow for movement of the socket relative to the monitor assembly. The ball and/or socket can be size, shaped and/or formed of a material that allows the ball to be inserted into and/or removed from the socket, and/or allows that socket to be inserted into and/or removed from the medical device for sanitary purposes. In one non-limiting arrangement, the ball and/or socket can be size, shaped and/or formed of a material that allows the ball to be inserted into and/or removed from the socket. In such an arrangement, the socket and/or ball can be fully or at least partially formed of a compressible material that facilitates in the insertion of the ball into and/or removal of the ball from the socket. The ball 520 includes an opening 530 that allow a syringe or other type of body penetrating device to be connected to the ball. The opening can be designed, sized and/or including an inner surface material that allows the syringe or other type of body penetrating device to be removably connected to the ball; however, this is not required. As can be appreciated, this mounting arrangement allows for multiple axes movement of the passageway penetration device. The opening in the ball can also be designed to allow for forward and backward movement of the passageway penetration device within the opening; however, this is not required. The socket can also or alternatively be designed to allow for forward and backward movement of the ball within the socket; however, this is not required.

The passageway penetration device can include one or more materials that enhance the viewing of the passageway penetration device on the one or more displays on the upper surface of the monitor assembly; however, this is not required. For instance, the needle on the syringe can be formed of and/or coated with a material that facilitates in identifying the needle, thus making it easier for a user to locate the needle on the one or more display screen. The electronic components of the medical device can also be designed to enhance the image of the needle (e.g., adjust brightness, adjust color, adjust size, etc.) on the one or more displays.

The operation of the medical device of FIGS. 1 and 2 will now be briefly described. Once the monitor assembly and support assembly are connected together, if such components were previously disconnected and/or folded in a compact form, the user raises the monitor assembly up from the base portion of the support assembly so that the body portion of the patient can be inserted between the monitor assembly and the support assembly. After the body portion is properly placed on the upper surface of the base portion, the monitor assembly is lowered onto the body portion. Contours in the base portion and monitor assembly, when used, facilitate in the proper positioning of the body portion between the base portion and the lower surface of the monitor assembly. A passageway penetration device such as a syringe is placed into the mount opening of the mount of the needle handling assembly. If the medical device is not already turned on, the user activate the power of the medical device so that the one or more displays on the upper surface of the monitor assembly turn on. The user, if not already accomplished, can enter in data in the monitor assembly and/or make other adjustments to the monitor assembly prior to the insertion of the needle of the syringe into the body portion, assuming that the monitor assembly is designed to have such information inputted. Once the one or more displays are powered, the user can adjust the position of the monitor device relative to the base portion so as to locate a desired body passageway such as a blood vessel in the body portion. Once the desired body passageway is located, the user can adjust the image on the one or more displays to enhance the displayed image, assuming that such features exist on the monitor assembly. The user then positions the syringe relative to the monitor assembly until the picture of the syringe needle on the one or more displays is positioned in a desired location relative to the body passageway in the body portion. The use can then more the syringe toward the monitor assembly to cause the needle to penetrate the body portion and access the desired body passageway. The needle can be continuously guided during this operation by the user viewing the image on the one or more displays. In this manner precise viewing and body passageway access is facilitated during operation and use by the medical device of the present invention.

In summary, the medical device of the present invention includes a monitor assembly that includes an image viewing surface, and a support assembly that is provided to position and/or secure the monitor assembly to a portion of a patient's body (e.g., arm, leg, etc.). Although the medical device is designed for particular use with human anatomy, it will be appreciated that the medical device of the present invention can be used on other types of living creatures (e.g., dogs, cats, horses, cattle, sheep, etc.). The support assembly includes a monitoring assembly securing portion. The monitoring assembly securing portion is designed to secure the monitor assembly to the support assembly. The monitoring assembly can be designed to releasably secure the monitoring assembly to the support assembly; however, this is not required. The support assembly can include an extremity securing portion that is designed to position a portion of a patient's body relative to the monitor assembly, the support assembly and needle handling assembly. The needle handling assembly is designed to guide a passageway penetration device such as a needle, catheter, etc. to a desired location in the patient's body. The basic operation, purpose and advantages of the medical device of the present invention are described in U.S. Pat. No. 6,443,928, which is incorporated fully herein by reference, thus will not be repeated herein.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

I claim:

1. A medical device designed to locate a body passageway on a patient to enable a user to access the body passageway in a body part of the patient, said medical device comprising a monitor assembly, a support assembly and a needle handling assembly, said monitor assembly including an upper and lower surface, said upper surface including at least one display designed to display a representation of the body passageway in the body portion that is positioned below said lower surface of said monitor assembly; said support assembly including a base portion and a side portion connected to said base portion, said base portion including an upper surface designed to receive the body portion of the patient, said side portion extending upwardly from said upper surface of said base portion, said side portion designed to at least partially support said monitor assembly above said upper surface of said base portion when the body portion is at least partially positioned between said base portion of said support assembly and said lower surface of said monitor assembly, said monitor assembly connected to said support assembly to enable said monitor assembly to move upwardly from or pivot upwardly from said upper surface of said base portion to enable the body portion to be positioned between said lower surface of said monitor assembly and said upper surface of said base portion of said support assembly, said monitor designed to produce the representation of the body passageway when said body portion is positioned between said base portion of said support assembly and said lower surface of said monitor assembly; said needle handling assembly designed to at least partially support one or more penetration devices selected from the group consisting of a needle, a catheter, a syringe, an IV and a tube, said needle handling assembly at least partially connected to said monitor assembly, said needle handling assembly designed to allow multi-axes positioning of said penetration device relative to the monitor assembly so as to enable a user to properly position an end of said penetration device relative to the body portion when attempting to access the body passageway while the user is viewing said display on said upper surface of said monitor assembly which is displaying said representation of the body passageway in the body portion while the body portion is positioned between said lower surface of said monitor assembly and said upper surface of said base portion of said support assembly.

2. The medical device as defined in claim 1, wherein said monitor assembly, said support assembly, or combinations thereof including one or more electronic components designed to process signals detected by one or more image receptors; said monitor assembly, said support assembly, or combinations thereof including one or more signal generators designed to generate an electromagnetic signal, an ultrasonic signal, or combinations thereof so that such signal at least partially contacts the body portion while the body portion is positioned between said lower surface of said monitor assembly and said upper surface of said base portion of said support assembly and is at least partially detected by one or more of said image receptors.

3. The medical device as defined in claim 1, wherein said monitor assembly is moveable along a longitudinal length of said support assembly.

4. The medical device as defined in claim 2, wherein said monitor assembly is moveable along a longitudinal length of said support assembly.

5. The medical device as defined in claim 1, wherein said monitor assembly is fully supported on one of said side walls of said support assembly.

6. The medical device as defined in claim 2, wherein said monitor assembly is fully supported on one of said side walls of said support assembly.

7. The medical device as defined in claim 1, wherein said upper surface of said base portion of said support assembly and said lower surface of said monitor device include a contoured surface designed to receive the body portion and at least partially position said body portion relative to said monitor assembly when said body portion is at least partially positioned between said support assembly and said monitor assembly.

8. The medical device as defined in claim 6, wherein said upper surface of said base portion of said support assembly and said lower surface of said monitor device include a contoured surface designed to receive the body portion and at least partially position said body portion relative to said monitor assembly when said body portion is at least partially positioned between said support assembly and said monitor assembly.

9. The medical device as defined in claim 1, wherein said base portion and said side wall of said support assembly are collapsible onto one another.

10. The medical device as defined in claim 8, wherein said base portion and said side wall of said support assembly are collapsible onto one another.

11. The medical device as defined in claim 1, wherein said monitor assembly is detachably connected to said support assembly.

12. The medical device as defined in claim 10, wherein said monitor assembly is detachably connected to said support assembly.

13. The medical device as defined in claim 1, wherein said monitor assembly, said support assembly, or combinations thereof include a solar panel, a fuel cell, or combinations thereof.

14. The medical device as defined in claim 12, wherein said monitor assembly, said support assembly, or combinations thereof include a solar panel, a fuel cell, or combinations thereof.

15. A medical device designed to locate a body passageway to enable a user to access the body passageway in a body portion of a patient, said medical device comprising a monitor assembly, a support assembly and a needle handling assembly, said monitor assembly including an upper and lower surface, said upper surface including at least one display designed to display a representation of the body passageway in a body portion that is positioned below said lower surface of said monitor assembly, said lower surface of said monitor assembly designed to receive information that can be processed to produce the representation of the body passageway; said support assembly including a base portion and a side portion connected to said base portion, said base portion including an upper surface designed to receive the body portion, said side portion extending upwardly from said upper surface of said base portion, said side portion designed to at least partially support said monitor assembly above said upper surface of said base portion when the body portion is at least partially positioned between said base portion of said support assembly and said lower surface of said monitor assembly, said monitor assembly connected to said support assembly to enable said monitor assembly to move upwardly from or pivot upwardly from said upper surface of said base portion to enable the body portion to be positioned between said lower surface of said monitor assembly and said upper surface of said base portion of said support assembly, said monitor designed to produce the representation of the body passageway when said body portion is positioned between said base portion of said support assembly and said lower surface of said monitor assembly, said monitor assembly, said support assembly, or combinations thereof including one or more electronic components designed to process signals detected by one or more image receptors, said monitor assembly, said support assembly, or combinations thereof including one or more signal generators designed to generate an electromagnetic signal, an ultrasonic signal, or combinations thereof so that such signal at least partially contacts the body portion while the body portion is positioned between said lower surface of said monitor assembly and said upper surface of said base portion of said support assembly and is at least partially detected by one or more of said image receptors, said monitor assembly is fully supported on one of said side walls of said support assembly, said monitor assembly is detachably connected to said support assembly; said needle handling assembly designed to at least partially support one or more penetration devices selected from the group consisting of a needle, a catheter, a syringe, an IV and a tube, said needle handling assembly at least partially connected to said monitor assembly, said needle handling assembly designed to allow multi-axes positioning of said penetration device relative to the monitor assembly so as to enable a user to properly position an end of said penetration device relative to the body portion when attempting to access the body passageway while the user is viewing said display on said upper surface of said monitor assembly which is displaying said representation of the body passageway in the body portion while the body portion is positioned between said lower surface of said monitor assembly and said upper surface of said base portion of said support assembly.

16. The medical device as defined in claim 15, wherein said upper surface of said base portion of said support assembly and said lower surface of said monitor device include a contoured surface designed to receive the body portion and at least partially position said body portion relative to said monitor assembly when said body portion is at least partially positioned between said support assembly and said monitor assembly.

17. The medical device as defined in claim 16, wherein said base portion and said side wall of said support assembly are collapsible onto one another.

18. The medical device as defined in claim 17, wherein said monitor assembly, said support assembly, or combinations thereof include a solar panel, a fuel cell, or combinations thereof.

19. A medical device designed to locate a blood vessel in an arm or leg of a patient so as to enable a user to insert a needle into the blood vessel, said medical device comprising a monitor assembly, a support assembly and a needle handling assembly, said monitor assembly including an upper and lower surface, said upper surface including at least one display designed to display a representation of the blood vessel in the arm or leg that is positioned below said lower surface of said monitor assembly, said lower surface of said monitor assembly designed to receive information that can be processed to produce the representation of the blood vessel; said support assembly including a base portion and a side portion connected to said base portion, said base portion including an upper surface designed to receive the arm or leg, said side portion extending upwardly from said upper surface of said base portion, said side portion designed to at least partially support said monitor assembly above said upper surface of said base portion so that the arm or leg can be positioned between said base portion of said support assembly and said lower surface of said monitor assembly, said monitor designed to produce the representation of the blood vessel when said arm or leg is positioned between said base portion of said support assembly and said lower surface of said monitor assembly, said monitor assembly connected to said support assembly to enable the arm or leg to be positioned between said lower surface of said monitor assembly and said upper surface of said base portion of said support assembly, said monitor assembly, said support assembly, or combinations thereof including one or more electronic components designed to process signals detected by one or more image receptors, said monitor assembly, said support assembly, or combinations thereof including one or more signal generators designed to generate an electromagnetic signal, an ultrasonic signal, or combinations thereof so that such signal at least partially contacts the arm or leg while the arm or leg is positioned between said lower surface of said monitor assembly and said upper surface of said base portion of said support assembly, said one or more image receptors at least partially detecting one or more signals generated by said one or more signal generators while the arm or leg is positioned between said lower surface of said monitor assembly and said upper surface of said base portion of said support assembly; said needle handling assembly designed to at least partially support a needle or device that includes a needle, said needle handling assembly at least partially connected to said monitor assembly, said needle handling assembly designed to allow multi-axis positioning of said penetration device relative to the monitor assembly so as to enable a user to properly position an end of said needle relative to the arm or leg when attempting to access the blood vessel on the patient while the user is viewing said display on said upper surface of said monitor assembly which is showing said representation of said blood vessel in the arm or leg while the arm or leg is positioned between said lower surface of said monitor assembly and said upper surface of said base portion of said support assembly.

20. The medical device as defined in claim 19, wherein said monitor assembly and said base portion are designed so that said monitor assembly can be fully supported on only one of said side walls of said support assembly while the arm or leg is positioned between said lower surface of said monitor assembly and said upper surface of said base portion of said support assembly.

21. The medical device as defined in claim 20, wherein said base portion and said side wall of said support assembly are collapsible onto one another, said monitor assembly is detachably connected to said support assembly, said monitor assembly connected to said support assembly to enable said monitor assembly to move upwardly from or pivot upwardly from said upper surface of said base portion to enable the arm or leg to be positioned between said lower surface of said monitor assembly and said upper surface of said base portion of said support assembly, said monitor designed to produce the representation of the blood vessel when said arm or leg is positioned between said base portion of said support assembly and said lower surface of said monitor assembly.

* * * * *